United States Patent [19]

Kasai et al.

[11] Patent Number: 5,246,843
[45] Date of Patent: Sep. 21, 1993

[54] PROCESS FOR PREPARATION OF R-(-)-3-HALOGENO-1,2,-PROPANEDIOL BY TREATMENT WITH MICROORGANISM

[75] Inventors: Naoya Kasai, Amagasaki; Toshio Suzuki, Toyonaka, both of Japan

[73] Assignee: Daiso Co., Ltd., Osaka, Japan

[21] Appl. No.: 8,824

[22] Filed: Jan. 25, 1993

Related U.S. Application Data

[63] Continuation of Ser. No. 630,046, Dec. 19, 1990, abandoned.

[30] Foreign Application Priority Data

Dec. 19, 1989 [JP] Japan ................................. 1-330367

[51] Int. Cl.$^5$ .......................... C12P 7/18; C12P 41/00; C12R 1/38; C12N 1/20
[52] U.S. Cl. ...................................... 435/158; 435/42; 435/253.3; 435/280; 435/874; 435/875; 435/876; 435/877
[58] Field of Search ...................... 435/42, 158, 253.3, 435/874, 875, 876, 877, 280

[56] References Cited

U.S. PATENT DOCUMENTS 5,017,484  5/1991  Nakamura et al. ................. 435/158

FOREIGN PATENT DOCUMENTS 0224246  3/1987  European Pat. Off. .
0207636  7/1987  European Pat. Off. .
0286059  12/1988  European Pat. Off. .
0317998  5/1989  European Pat. Off. ............ 435/158
3-053886  3/1991  Japan .................................. 435/158

Primary Examiner—Herbert J. Lilling
Attorney, Agent, or Firm—Sherman and Shalloway

[57] ABSTRACT

A process for preparation of R-(−)-3-halogeno-1,2-propanediol which comprises cultivating in a medium containing racemate 3-halogeno-1,2-propanediol a bacterium, which, when cultivated in a medium containing racemate 3-halogeno-1,2-propanediol as a sole carbon source, can grow and proliferate, has an ability to assimilate S-(+)-3-halogeno-1,2-propanediol preferentially compared to R-(−)-3-halogeno-1,2-propanediol and belongs to the genus Pseudomonas, or its culture cells; and recovering R-(−)-3-halogeno-1,2-propanediol from the resulting culture broth.

13 Claims, No Drawings

PROCESS FOR PREPARATION OF R-(-)-3-HALOGENO-1,2,-PROPANEDIOL BY TREATMENT WITH MICROORGANISM

This application is a continuation of application Ser. No. 07/630,046, filed Dec. 19, 1990, now abandoned.

DETAILED DESCRIPTION OF THE INVENTION

1. Industrially Applicable Field

This invention relates to a process for separatively obtaining optically active R-(−)-3-halogeno-1,2-propanediol from racemate 3-halogeno-1,2-propanediol using a microorganism.

This invention further relates to a pure culture of a bacterium belonging to the genus Pseudomonas having the ability to assimilate S-(+)-3-halogeno-1,2-propanediol preferentially compared to R-(−)-3-halogeno-1,2-propanediol.

2. Prior Art

R-(−)-3-halogeno-1,2-propanediol is a useful substance as a raw material for synthesis of optically active pharmaceuticals and physiologically active substances. R-(−)-3-halogeno-1,2-propanediol can, for example, be utilized for synthesis of optically active beta-adrenergic blockers, L-carnitine and the like. Further, R-(−)-3-halogeno-1,2-propanediol can be converted to R-(+)-glycidol, a useful intermediate for synthesis of optically active pharmaceuticals and pesticides as well as physiologically active substances and Ferroelectric Liquid Crystals.

As processes for preparation of this useful R-(−)-3-halogeno-1,2-propanediol the following processes have hitherto been known.

The process of Hayan F. Jones to obtain it from methyl-5-chloro-5-deoxy-alpha-L-arabinofuranoside (Chemistry and Industry, 15, P533, 1978) and the process of H. Jackson, et al. to obtain it from 1,2,5,6-diacetonyl-D-mannitol (Chem.-Biol. Interaction, 13, P193, 1976) are chemical synthetic processes, and, in both cases, the raw materials are hard to obtain, high synthetic technique is necessitated and the steps are complicated, and thus these processes are industrially unsuitable.

On the other hand, Takahashi et al. proposed a process to obtain optically active 3-chloro-1,2-propanediol using a microorganism (European Laid-Open Patent Publication Nos. 0224246 and 0286059).

In this process of using a microorganism, extremely many kinds of microorganisms are proposed and several microorganisms belonging to the genus Pseudomonas are included among them. These processes mainly utilize the reaction that S-(+)-3-halogeno-1,2-propanediol is oxidatively decomposed and metabolized by action of a microorganism. However, these processes have the following problems.

Although *Pseudomonas fragi* IFO 3458, *Pseudomonas crucicuiae* IFO 12047 and *Pseudomonas chlororaphis* IFO 3904 disclosed in the above European Laid-Open Patent Publication No. 0224246 can metabolize S-(+)-3-halogeno-1,2-propanediol, as is the case with other microorganisms, they cannot grow and proliferate in a completely synthetic medium containing racemate 3-halogeno-1,2-propanediol as a sole carbon source and an inorganic nitrogen such as ammonium sulfate or ammonium nitrate as a nitrogen source.

Therefore, when reaction is carried out utilizing any of the above microorganisms, the process must be adopted which comprises proliferating the cells in advance in a nutrient medium to obtain lots of cells and making the cells after washing act on racemate 3-halogeno-1,2-propanediol, as disclosed in the examples of the above patent. If the above process is not adopted, it becomes necessary to add racemate 3-halogeno-1,2-propanediol in a medium which contains other nutrients and wherein the microorganism can grow, and this latter process is not a preferred process in view of reaction efficiency or purification of the product.

Problem to be Solved by the Invention

Thus, the object of the invention is to provide a process capable of preparing highly pure R-(−)-3-halogeno-1,2-propanediol economically, inexpensively and technically simply, compared to the aforesaid usual processes.

Means for Solving the Problem

As a result of vigorous studies to find a microorganism which can assimilate S-(+)-3-halogeno-1,2-propanediol preferentially compared to R-(-)-3-halogeno-1,2-propanediol and can grow and proliferate when cultivated in a medium containing racemate 3-halogeno-1,2-propanediol as a sole carbon source, the present inventors succeeded in isolation from the soil a microorganism capable of attaining the above object of the invention and accomplished the invention.

Thus, the invention provides a process for preparation of R-(−)-3-halogeno-1,2-propanediol which comprises cultivating in a medium containing racemate 3-halogeno-1,2-propanediol a bacterium, which, when cultivated in a medium containing racemate 3-halogeno-1,2-propanediol as a sole carbon source, can grow and proliferate, has an ability to assimilate S-(+)-3-halogeno-1,2-propanediol preferentially compared to R-(−)-3-halogeno-1,2-propanediol and belongs to the genus Pseudomonas, or its culture cells; and recovering R-(−)-3-halogeno-1,2-propanediol from the resulting culture broth.

According to the process of the invention, even when mass production or R-(−)-3-halogeno-1,2-propanediol is undertaken, there is no need to cultivate a large number of cells separately and collect the resulting cells, and it is sufficient to cultivate the bacterium in an amount enough as a seed strain and inoculate it into the medium.

In assimilation of S-(+)-3-halogeno-1,2-propanediol by any of the bacteria which can be used in the invention and belong to the genus Pseudomonas, dehydrohalogenation reaction of S-(+)-3-halogeno-1,2-propanediol is carried out and as a result hydrohalogenic acid is formed.

Suitable as 3-halogeno-1,2-propanediols used in the invention are 3-chloro-1,2-propanediol and 3-bromo-1,2-propanediol.

The morphological and physiological properties of the three representative bacteria, which were isolated and recovered from the soil by the inventors and can be used in the invention, are set forth below in Table 1.

TABLE 1

| | Pseudomonas sp. DS-K-2D1 | Pseudomonas sp. DS-K-9D1 | Pseudomonas sp. DS-K-14A4 |
|---|---|---|---|
| A. Morphology | | | |
| 1. Shape of cells | rods | same as left | same as left |
| 2. Size of cells | 0.4–0.6 × 1.2–1.5 μm | same as left | same as left |
| 3. Pleomorphisms cells | none | same as left | same as left |
| 4. Mobility | +, polar flagella | same as left | same as left |
| 5. Spores | none | same as left | same as left |
| 6. Gram stain | negative | same as left | same as left |
| 7. Acid fastness | none | same as left | same as left |
| B. Growth condition in various media | | | |
| 1. Nutrient agar (3 days at 30° C.) | | | |
| 1) Speed of colony growth | ordinary | same as left | same as left |
| 2) Shape of colonies | circular | same as left | same as left |
| 3) Shape of colony surface | smooth | same as left | same as left |
| 4) Raised condition of colonies | convex | same as left | same as left |
| 5) Periphery of colonies | entire | same as left | same as left |
| 6) Contents of colonies | homogeneous | same as left | same as left |
| 7) Color of colonies | milky white | same as left | same as left |
| 8) Gloss of colonies | dull | same as left | same as left |
| 9) Transparency of colonies | translucent | same as left | same as left |
| 10) Formation of soluble pigments | none | same as left | same as left |
| 2. Slant culture of nutrient agar (for 3 days at 30° C.) | | | |
| 1) Growth degree | good | same as left | same as left |
| 2) Growth condition | filiform | same as left | same as left |
| 3) Shape of colony surface | smooth | same as left | same as left |
| 4) Shape of colonies in section | flat | same as left | same as left |
| 5) Gloss of colonies | dull | same as left | same as left |
| 6) Color tone of colonies | milky white | same as left | same as left |
| 7) Transparency of colonies | translucent | same as left | same as left |
| 3. Nutrient liquid standing culture (for 3 days at 30° C.) | | | |
| 1) Growth condition | somewhat turbid | same as left | same as left |
| 2) Gas production | none | same as left | same as left |
| 3) Coloring of the medium | none | same as left | same as left |
| 4. Gelatin liquefaction test (+: liquefacts gelatin, −: liquefacts no gelatin) | − | − | − |
| 5. Litmus milk (+: reduces litmus to white, non-coagulated, −: no change, non-coaculated) | + | − | + |
| 6. MGPB agar (for 6 days at 30° C.) (MGPB agar: 3-halogeno-1,2-propanediol 1.0%, peptone 0.1%, yeast extract 0.1%, Bromothymol Blue 0.01%, agar 2.0%, pH 7.0) | | | |
| 1) Spped of colony growth | slow | same as left | same as left |
| 2) Shape of colonies | circular | same as left | same as left |
| 3) Shape of colony surface | smooth | wrinkled (radial) | smooth |
| 4) Raised condition of colonies | uumbonate | convex | convex |
| 5) Periphery of colonies | entire | same as left | same as left |
| 6) Contents of colonies | homogeneous | same as left | same as left |
| 7) Color of colonies | orange at the center white at the periphery | same as left | same as left |
| 8) Gloss of colonies | dull | same as left | same as left |
| 9) Transparency of colonies | opaque | same as left | same as left |
| 10) Formation of soluble pigments | none | same as left | same as left |
| C. Physiological test | | | |
| 1. Lysine decarboxylation test | + | + | + |
| 2. VP test | − | − | − |
| 3. MR test | − | − | − |
| 4. Reduction of nitrate | − | − | − |
| 5. Production of indole | − | − | − |
| 6. PPA reaction | − | − | − |
| 7. Formation of hydrogen sulfide | − | − | − |
| 8. Utilization of citric acid | + | + | + |
| 9. Starch decomposition test | − | − | − |
| 10. Denitrification reaction | − | − | − |
| 11. Utilization of inorganic salt | + | + | + |
| 12. Formation of dye | | | |
| 1) King A medium | − | − | − |
| 2) King B medium | − | − | − |
| 3) Pseudomonas P medium | − | − | − |
| 4) Peseudomonas F medium | − | − | − |
| 13. Catalase | + | + | + |
| 14. Oxidase | + | + | + |

TABLE 1-continued

|  |  | Pseudomonas sp. DS-K-2D1 | Pseudomonas sp. DS-K-9D1 | Pseudomonas sp. DS-K-14A4 |
|---|---|---|---|---|
| 15. | Arginine dehydrogenase | — | — | — |
| 16. | Urease test | — | — | — |
| 17. | OF-test (Hugh Leifson method. No gas formation was observed.) | | | |
|  | 1) D-glucose | O | O | O |
|  | 2) Glycerol | O | O | O |
|  | 3) D-galactose | O | O | O |
|  | 4) D-fructose | O | O | O |
|  | 5) D-trehalose | O | O | O |
| 18. | Accumulation of PHB | + | + | + |
| 19. | Utilization of carbon sources | | | |
|  | 1) D-mannitol | + | + | + |
|  | 2) D-fructose | + | + | + |
|  | 3) D-glucose | + | + | + |
|  | 4) D-gluconic acid | + | + | + |
|  | 5) D-galactose | + | + | + |
|  | 6) Glycerol | + | + | + |
|  | 7) p-Hydroxybenzoic acid | + | + | + |

By classification based on the results of Table 1 according to Bergey's Manual of Systematic Bacteriology 9th edition, it was revealed that all the above strains belong to the genus Pseudomonas because they are Gram-negative aerobic rods, have polar flagella, and are oxidase-positive and catalase-positive. Although there can be mentioned as their closely related strains Pseudomonas acidoborans, Pseudomonas testosteroni, Pseudomonas delafieldii, Pseudomonas facilis, Pseudomonas saccharophila, Pseudomonas flava, Pseudomonas pseudoflava and Pseudomonas palleronii, the above strains differs from Pseudomonas acidoborans and Pseudomonas testosteroni in that all the former strains can utilize D-glucose as a carbon source whereas the latter strains cannot utilize D-glucose as a carbon source, from Pseudomonas delafieldii, Pseudomonas facilis, Pseudomonas saccharophila and Pseudomonas flava in that all the former strains can utilize p-hydroxybenzoate as a carbon source whereas the latter strains cannot utilize p-hydroxybenzoate as a carbon source, and from Pseudomonas pseudoflava and Pseudomonas palleronii in that all the former strains form no carotenoid pigment whereas the latter strains form carotenoid pigments. Thus, all the above strains do not accord with the known strains in characteristics, and were believed to be novel strains and named Pseudomonas sp. DS-K-2D1, Pseudomonas sp. DS-K-9D1 and Pseudomonas sp. DS-K-14A4.

Further, although these strains are mutually analogous strains each belonging to the genus Pseudomonas, Pseudomonas sp. DS-K-2D1 and Pseudomonas sp. DS-K-14A4 differ from Pseudomonas sp. DS-K-9D1 in that the former strains reduce litmus milk to white whereas the later strain does not reduce litmus milk to white, and Pseudomonas sp. DS-K-2D1 differs from Pseudomonas sp. DS-K-14A4 in that, in the growth condition in the MGPB agar, the raised condition of colonies is convex at the center in the former whereas the raised condition of colonies is convex in the latter. Thus, the above strains were found as three mutually different strains.

The above three strains were deposited with Fermentation Research Institute, Agency of Industrial Science and Technology, Japan on Nov. 15, 1989, and, thereafter, their control was transferred in the Fermentation Research Institute on Sep. 12, 1990 in accordance with Budapest Treaty on the international recognition of the deposit of microorganism for the purpose of patent procedure. Deposit numbers of the respective strains are set forth below.

|  | Pseudomonas sp. DS-K-2D1 | Pseudomonas sp. DS-K-9D1 | Pseudomonas sp. DS-K-14A4 |
|---|---|---|---|
| FRI (Nov. 15, 1989) | FERM P-11109 | FERM P-11108 | FERM P-11110 |
| FRI under Budapest Treaty (Sep. 12, 1990) | FERM BP-3096 | FERM BP-3095 | FERM BP-3097 |

Strains which can be used in the invention and belong to the genus Pseudomonas are not limited to the above three strains. Namely, other strains can similarly be used so long as they have an ability to assimilate S-(+)-3-halogeno-1,2-propanediol preferentially compared to R-(−)-3-halogeno-1,2-propanediol and can grow and proliferate in a medium containing racemate 3-halogeno-1,2-propanediol as a sole carbon source.

Specifically, the process of the invention can be carried out either by cultivating any of the above bacteria in a synthetic medium containing racemate 3-halogeno-1,2-propanediol as a substantially sole carbon source, inorganic nitrogens (various ammonium salts or nitrates) as nitrogen sources and further inorganic salts, and recovering the remaining R-(−)-3-halogeno-1,2-propanediol from the culture broth, or by cultivating any one of the above bacteria in a medium containing carbon sources, nitrogen sources, organic nutrient sources and inorganic sources and usually frequently used, for example, a bouillon medium or a peptone medium, inoculating the thus obtained culture broth or culture cells into a medium containing racemate 3-halogeno-1,2-propanediol as a sole carbon source, further carrying out cultivation or making the cells act, and then recovering the remaining R-(−)-3-halogeno-1,2-propanediol from the culture broth.

As carbon sources, there can be used, besides racemate 3-halogeno-1,2-propanediol, alcohols such as glycerol, saccharides such as D-glucose, D-fructose and D-galactose, and organic acids such as citric acid, maleic acid, malic acid and fumaric acid and their salts.

It is advantageous in the process of the present invention to use racemate 3-halogeno-1,2-propanediol as the substantial carbon source.

Further, as nitrogen sources there can be used those usually used in cultivation of cells. Examples thereof include inorganic nitrogens such as ammonium sulfate, ammonium nitrate and ammonium phosphate, and organic nitrogens such as urea, peptone, casein, yeast extract, meat extract and corn steep liquor. There can further be used generally known inorganic salts such as phosphates, magnesium salts, potassium salts, manganese salts, zinc salts and copper salts.

Cultivation of the invention can be carried out by conventional conditions and means. Namely, the cultivation is carried out at a cultivation temperature of about 20° to 40° C., preferably 25° to 37° C., at a pH of about 5 to 10, preferably 5.5 to 9.5 and under an aerobic condition, using a means of shaking cultivation or aeration stirring cultivation on the like. The substrate concentration in the reaction mixture is preferably on the order of 0.1 to 10% (v/v), and although the reaction time varies depending on the substrate concentration and other reaction conditions, it is preferably 48 to 80 hours. It is preferred that the reaction is discontinued at the time when the remaining substrate analyzed by gas chromatography or the like was reduced up to 50%, namely at the time when S-(+)-3-halogeno-1,2-propanediol was substantially assimilated. Recovery and purification of the remaining R-(−)-3-halogeno-1,2-propanediol can be carried out as follows. Namely, the purification and recovery can be carried out by separating the culture broth after completion of the cultivation into the microbial cells and the supernatant by centrifugation, a flocculant agent or the like, adsorbing on active carbon R-(−)-3-halogeno-1,2-propanediol remaining in the supernatant, and then either eluting it with acetone and then subjecting the eluate to vacuum distillation, or extracting it with a solvent such as ethyl acetate and then subjecting the extract to vacuum distillation.

The S-(+)-3-halogeno-1,2-propanediol-assimilating strains belonging to the genus Pseudomonas in the invention are novel, and their pure cultures are also provided by the invention. As these strains, there can particularly preferably be used those named Pseudomonas sp. DS-K-9D1, Pseudomonas sp. DS-K-2D1 and Pseudomonas sp. DS-K-14A4.

EXAMPLE

The invention is specifically described below by examples. % in the examples indicates % by weight unless otherwise noted.

EXAMPLE 1

100 ml of a medium having the composition of

| | |
|---|---|
| ammonium sulfate | 0.5% |
| disodium hydrogenphosphate | 0.1% |
| dipotassium hydrogenphosphate | 0.1% |
| sodium dihydrogenphosphate | 0.2% |
| magnesium sulfate | 0.05% |
| iron sulfate, copper sulfate and manganese sulfate | trace |
| calcium carbonate | 0.45% |
| pH 6.8 | | poured in a 500-ml Sakaguchi flask was sterilized at 121° C. for 15 minutes, and then racemate 3-chloro-1,2-propanediol was added thereto to 1.0% (v/v) to prepare a medium containing racemate 3-chloro-1,2-propanediol as a sole carbon source. One platinum loopful of a slant agar culture of Pseudomonas sp. DS-K-2D1, one of the microorganisms shown in Table 1, was inoculated into the above medium and cultivated with shaking for 4 days under the conditions of 30° C. and 130 rpm.

After completion of the cultivation, the culture broth was taken out and subjected to centrifugation to remove the cells and obtain the supernatant. This supernatant was concentrated up to about 20 ml and the concentrate was extracted with ethyl acetate. The extract was dehydrated with anhydrous magnesium sulfate and kept under reduced pressure to obtain 0.4 g of 3-chloro-1,2-propanediol as an oily substance.

Identification of this substance was carried out by gas chromatography. When the substance was compared with commercially available racemate 3-chloro-1,2-propanediol (product of Tokyo Kasei Co.) using a column carrier PEG-20MP, 60–80 mesh, the retention times of both substances were utterly identical.

The specific rotation of the present substance and the specific rotation of (R)-3-chloro-1,2-propanediol (literature value) are as follows.

| | |
|---|---|
| The present substance | $[\alpha]_D^{22} = -7.75°$ |
| | (C = 1, H$_2$O) |
| Literature value | $[\alpha]_D^{22} = -6.9°$ |
| | (C = 2, H$_2$O) |

Further, after the present substance was tosylated according to a conventional method, HPLC analysis was carried out under the conditions of room temperature, a flow rate of 1.0 ml/min and a wavelength of 235 nm using an optical isomer-separating column [CHIRALCEL OC column (25 cm×0.46 cm I.D.)] (produced by DAICEL CHEMICAL INDUSTRIES, LTD.) and hexane-isopropanol (95:5) as a solvent. Retention times by this analytic method are 79 minutes for the S form compound and 89.8 minutes for the R form compound, and the present substance exhibited a retention time corresponding to that of the R form compound and its enantiomer excess was 98% e.e. or more.

EXAMPLES 2 AND 3

The same operations as in Example 1 were carried out except that the strain was replaced by Pseudomonas sp. DS-K-9D1 or Pseudomonas sp. DS-K-14A4. When analyzed according to the various analytical methods as shown in Example 1, each of the obtained substances was revealed to be R-(−)-3-chloro-1,2-propanediol having an enantiomer excess of 98% e.e. or more. The results of Examples 2 and 3 are shown together below.

| Example No. | Strain | $[\alpha]_D^{22}$ (C = 1, H$_2$O) | Yield (g) |
|---|---|---|---|
| 2 | DS-K-9D1 | −7.70° | 0.38 |
| 3 | DS-K-14A4 | −7.71° | 0.45 |

EXAMPLE 4

2.5 l of the medium having the composition of

| | |
|---|---|
| ammonium sulfate | 0.5% |
| disodium hydrogenphosphate | 0.02% |
| dipotassium hydrogenphosphate | 0.02% |
| sodium dihydrogenphosphate | 0.04% |

| | |
|---|---|
| magnesium sulfate | 0.05% |
| iron sulfate, copper sulfate and manganese sulfate | trace |
| pH 6.8 | | poured in a 5-liter cultivation apparatus (jar fermentor) was sterilized at 121° C. for 15 minutes, and then racemate 3-chloro-1,2-propanediol was added thereto to 1.0% (v/v) to prepare a medium containing racemate 3-chloro-1,2-propanediol as a sole carbon source. Then, Pseudomonas sp. DS-K-2D1, one of the microorganisms indicated in Table 1, was previously cultivated with shaking at 30° C. for 24 hours in a nutrient medium comprising 1.0% of peptone, 1.0% of yeast extract and 1.0% of glycerol, pH 7.2, and the culture broth was aseptically inoculated into the above medium containing racemate 3-chloro-1,2-propanediol as a sole carbon source so that its amount became 2% (v/v). Aerobic stirring cultivation was carried out for 4 days under the following conditions:

| | |
|---|---|
| Temperature | 30° C. |
| Aeration amount | 0.5 1/min |
| agitation | 500 rpm |

Measurement and control of pH were carried out by a linked pH meter and the pH was controlled at 6.8 with 3N-NaOH.

After completion of the cultivation, the culture broth was taken out and subjected to centrifugation to remove the cells and obtain the supernatant. The supernatant was treated in the same manner as in Example 1 to obtain 14.9 g of 3-chloro-1,2-propanediol. The obtained substance was subjected to the various analyses as shown in Example 1, and as a result it was revealed that the substance was R-(−)-3-chloro-1,2-propanediol having an enantiomer excess of 98% e.e. or more. The specific rotation $[\alpha]_D^{22}$ of this substance was $-7.75°$ (C=1, H$_2$O).

EXAMPLES 5 and 6

The same operations as in Example 4 were carried out except that the strain was replaced by Pseudomonas sp. DS-K-9D1 or Pseudomonas sp. DS-K-14A4 shown in Table 1. By the various analyses shown in Example 1, each of the obtained substances was revealed to be R-(−)-3-chloro-1,2-propanediol having an enantiomer excess of 98% e.e. or more. The results of Examples 5 and 6 are shown below in a lump.

| Example No. | Strain | $[\alpha]_D^{22}$ (C = 1, H$_2$O) | Yield (g) |
|---|---|---|---|
| 5 | DS-K-9D1 | −7.74° | 15.0 |
| 6 | DS-K-14A4 | −7.70° | 13.5 |

EXAMPLE 7

100 ml of a nutrient medium having the composition of 1.0% of peptone, 1.0% of yeast extract and 1.0% of glycerol, pH 7.2 in a 500-ml Sakaguchi flask was sterilized at 121° C. for 15 minutes, and then one platinum loopful of a slant agar culture of Pseudomonas sp. DS-K-2D1 shown in Table 1 was inoculated thereinto. Cultivation was carried out at 30° C. for 24 hours with shaking, the cells and the supernatant were separated by centrifugation and the supernatant was discarded. The resulting cells were washed a few times with a 50 mM phosphate buffer, pH 7.0. The cells were then suspended in 100 ml of the medium containing racemate 3-chloro-1,2-propanediol as a sole carbon source shown in Example 1, and reaction was carried out at 30° C. and 130 rpm for 3 days. After completion of the reaction, the cells were removed by centrifugation to obtain the supernatant. The supernatant was treated in the same manner as in Example 1 to obtain 0.4 g of 3-chloro-1,2-propanediol. The substance was subjected to the various analyses as shown in Example 1, and as a result it was revealed that the substance was R-(−)-3-chloro-1,2-propanediol having an enantiomer excess of 98% e.e. or more. The specific rotation $[\alpha]_D^{22}$ of the substance was $-7.75°$ (C=1, H$_2$O).

EXAMPLES 8 AND 9

The same operations as in Example 7 were carried out except that the strain was replaced by Pseudomonas sp. DS-K-9D1 or Pseudomonas sp. DS-K-14A4 shown in Table 1. By the various analyses as shown in Example 1, each of the obtained substances was revealed to be R-(−)-3-chloro-1,2-propanediol having an enantiomer excess of 98% e.e. or more. The results of Examples 8 and 9 are shown below in a lump.

| Example No. | Strain | $[\alpha]_D^{22}$ (C = 1, H$_2$O) | Yield (g) |
|---|---|---|---|
| 8 | DS-K-9D1 | −7.74° | 0.51 |
| 9 | DS-K-14A4 | −7.70° | 0.45 |

EXAMPLES 10 to 12

The same experiments as in Examples 1 to 3 were carried out except that racemate 3-chloro-1,2-propanediol was replaced by racemate 3-bromo-1,2-propanediol. Experimental methods and other operations were carried out according to Example 1. The results of Examples 10 to 12 are shown below in a lump.

| Example No. | Strain | $[\alpha]_D^{22}$ (C = 1, H$_2$O) | Yield (g) |
|---|---|---|---|
| 10 | DS-K-2D1 | −3.80° | 0.61 |
| 11 | DS-K-9D1 | −3.75° | 0.65 |
| 12 | DS-K-14A4 | −3.77° | 0.55 |

In this connection, the literature value of the specific rotation of (R)-3-bromo-1,2-propanediol is as follows:

$[\alpha]_D^{25} = -3.94°$ (C=5.07, CHCl$_3$).

Further, each of R-(−)-3-bromo-1,2-propanediols obtained by Examples 10 to 12 was tosylated by a conventional manner, and the tosylated compound was subjected to HPLC analysis under the conditions of room temperature, a flow rate of 1.0 ml/min and a wavelength of 235 nm using an optical isomer-separating column [CHIRALCEL, OC column (25 cm×0.46 cm I.D.)] (produced by DAICEL CHEMICAL INDUSTRIES, LTD.) and hexane-isopropanol (95:5) as a solvent. Retention times in this analysis are 98.9 minutes for the S-form compound and 115.4 minutes for the R-form compounds, and each of the above substances exhibited a retention time corresponding to the R-form compound and had an enantiomer excess of 96% e.e. or more.

EXAMPLES 13 to 15

Experiments were carried out in accordance with Examples 4 to 6 except that racemate 3-chloro-1,2-propanediol was replaced by racemate 3-bromo-1,2-propanediol. Experimental methods and other operations were carried out according to Example 4. By the various analyses as shown in Example 10, each of the obtained substances was revealed to be R-(−)-3-bromo-1,2-propanediol having an enantiomer excess of 96% e.e. or more. The results of Examples 13 to 15 are shown below in a lump.

| Example No. | Strain | $[\alpha]_D^{22}$ (C = 1, H$_2$O) | Yield (g) |
|---|---|---|---|
| 13 | DS-K-2D1 | 3.77° | 17.1 |
| 14 | DS-K-9D1 | −3.74° | 15.5 |
| 15 | DS-K-14A4 | −3.78° | 16.8 |

EXAMPLES 16 to 18

Experiments were carried out in accordance with Examples 7 to 9 except that racemate 3-chloro-1,2-propanediol was replaced by racemate 3-bromo-1,2-propanediol. Experimental methods and other operations were carried out according to Example 7. By the various analyses as shown in Example 10, each of the obtained substances was revealed to be R-(−)-3-bromo-1,2-propanediol having an enantiomer excess of 96% e.e. or more. The results of Examples 16 to 18 are shown below in a lump.

| Example No. | Strain | $[\alpha]_D^{22}$ (C = 1, H$_2$O) | Yield (g) |
|---|---|---|---|
| 16 | DS-K-2D1 | −3.77° | 0.62 |
| 17 | DS-K-9D1 | −3.78° | 0.59 |
| 18 | DS-K-14A4 | −3.74° | 0.66 |

Effects of the Invention

In accordance with the invention, it is possible to prepare R-(−)-3-halogeno-1,2-propanediol by a method wherein inexpensive raw materials can be utilized and which is industrially convenient, namely by assimilating S-(+)-3-halogeno-1,2-propanediol preferentially from racemate 3-halogeno-1,2-propanediol utilizing a bacterium of the genus Pseudomonas.

We claim:

1. A process for preparation of R-(−)-3-chloro-1,2-propanediol or R-(−)-3-bromo-1,2-propanediol which comprises cultivating and proliferating, in a medium containing racemate 3-chloro-1,2-propanediol or racemate 1-bromo-1,2-propanediol as an essential carbon source, a bacterium belonging to the genus Pseudomonas which is selected from the group consisting of Pseudomonas sp. DS-K-9D1, Pseudomonas sp. DS-K-2D1 and Pseudomonas sp. DS-K-14A4 which are deposited with Fermentation Research Institute, Agency of Industrial Science and Technology, Japan as Deposit Nos. FERM BP-3095, FERM BP-3096 and FERM BP-3097, respectively, or its culture cell, and recovering R-(−)-3-chloro-1,2-propanediol or R-(−)-3-bromo-1,2-propanediol from the resulting culture broth.

2. The process of claim 1 in which each of said bacteria has the ability to grow and proliferate when cultivated in a medium containing racemate 3-chloro-1,2-propanediol or racemate 3-bromo-1,2-propanediol as the sole carbon source.

3. The process of claim 1 for preparing R-(−)-3-chloro-1,2-propanediol wherein the medium contains racemate 3-chloro-1,2-propanediol.

4. The process of claim 1 for preparing R-(−)-3-chloro-1,2-propanediol wherein the medium contains racemate 3-bromo-1,2-propanediol.

5. The process of claim 1 wherein the cultivation is carried out under an aerobic condition.

6. The process of claim 1 wherein the cultivation is carried out at a temperature of about 20° C. to about 40° C.

7. The process of claim 1 wherein the cultivation is carried out at a pH of about 5 to about 10.

8. The process of claim 1 wherein the bacterium is Pseudomonas sp. DS-K-9D1.

9. The process of claim 1 wherein the bacterium is Pseudomonas sp. DS-K-2D1.

10. The process of claim 1 wherein the bacterium is Pseudomonas sp. DS-K-14A4.

11. The process of claim 1 wherein the cultivation is carried out under aerobic conditions at a temperature of from about 25° to 37° C. at a pH of from about 5.5 to 9.5 at a substrate concentration in the reaction mixture of from 0.1 to 10% (v/v) for from about 48 to 80 hours.

12. The process of claim 11 wherein the cultivation is carried out in a medium containing racemate 3-chloro-1,2-propanediol as the sole carbon source.

13. The process of claim 1 in which the cultivation is carried out in a medium containing racemate 3-bromo-1,2-propanediol as the sole carbon source.

* * * * *